United States Patent
Wyatt (10) Patent No.: US 8,010,386 B2
(45) Date of Patent: Aug. 30, 2011

(54) METHOD AND A SYSTEM FOR EFFECTING TRANSFER OF A PATIENT FROM A HOSPITAL VIA A COMPUTER NETWORK

(75) Inventor: Phil Wyatt, Lake Forest, IL (US)

(73) Assignee: Medical Central Online, Lake Forest, IL (US)

( * ) Notice: Subject to any disclaimer, the term of this patent is extended or adjusted under 35 U.S.C. 154(b) by 2768 days.

(21) Appl. No.: 10/736,373

(22) Filed: Dec. 15, 2003

(65) Prior Publication Data

US 2004/0128168 A1 Jul. 1, 2004

Related U.S. Application Data (63) Continuation-in-part of application No. 09/544,508, filed on Apr. 6, 2000, now Pat. No. 7,539,623.

(51) Int. Cl.
*G06Q 40/00* (2006.01)
(52) U.S. Cl. .............. 705/4; 705/2; 705/3; 600/300
(58) Field of Classification Search .............. 705/2, 3, 705/4; 600/300
See application file for complete search history.

(56) References Cited

U.S. PATENT DOCUMENTS

| | | | |
|---|---|---|---|
| 4,135,241 A | 1/1979 | Stanis et al. | |
| 4,491,725 A * | 1/1985 | Pritchard | 705/2 |
| 5,253,164 A * | 10/1993 | Holloway et al. | 705/2 |
| 5,669,005 A | 9/1997 | Curbow et al. | |
| 5,717,945 A | 2/1998 | Tamura | |
| 5,781,442 A * | 7/1998 | Engleson et al. | 700/214 |
| 5,784,625 A | 7/1998 | Walker | |
| 5,809,477 A * | 9/1998 | Pollack | 705/3 |
| 5,826,237 A | 10/1998 | Macrae et al. | |
| 5,835,712 A | 11/1998 | DuFresne | |
| 5,848,427 A | 12/1998 | Hyodo | |
| 5,878,262 A | 3/1999 | Shoumura et al. | |
| 5,884,321 A | 3/1999 | Meffert | |
| 5,911,145 A | 6/1999 | Arora et al. | |
| 5,933,828 A | 8/1999 | Eitel et al. | |
| 5,940,834 A | 8/1999 | Pinard et al. | |
| 5,950,207 A | 9/1999 | Mortimore et al. | |
| 5,953,724 A | 9/1999 | Lowry | |
| 5,956,704 A | 9/1999 | Gautam et al. | |
| 5,956,720 A | 9/1999 | Fernandez et al. | |
| 5,956,737 A | 9/1999 | King et al. | |
| 5,966,717 A | 10/1999 | Sass | |
| 5,974,430 A | 10/1999 | Mutschler, III et al. | |
| 5,974,431 A | 10/1999 | Iida | |
| 5,983,227 A | 11/1999 | Nazem et al. | |
| 5,991,534 A | 11/1999 | Hamilton et al. | |
| 5,995,937 A | 11/1999 | DeBusk et al. | |
| 6,014,632 A * | 1/2000 | Gamble et al. | 705/4 |
| 6,026,363 A | 2/2000 | Shepard | |
| 6,026,417 A | 2/2000 | Ross et al. | |

(Continued)

*Primary Examiner* — Lena Najarian
(74) *Attorney, Agent, or Firm* — Patents + TMS, P.C.

(57) ABSTRACT

A method and a system for provides bed availability information via a computer network. A healthcare facility may provide bed availability and/or service information to a database on a computer network. Users of the computer network may access the information within the database. The healthcare facility may create a transfer request form for discharge of a patient to an extended care facility. The transfer request form containing patient medical information and/or patient treatment information is reviewed by an agent. The agent decides whether to approve the transfer request. Notifications are sent to the parties involved with the discharge of the patient to the healthcare facility notifying the parties of the decision of the agent.

14 Claims, 4 Drawing Sheets

U.S. PATENT DOCUMENTS

| | | | |
|---|---|---|---|
| 6,032,119 A | 2/2000 | Brown et al. | |
| 6,035,276 A | 3/2000 | Newman et al. | |
| 6,055,506 A * | 4/2000 | Frasca, Jr. | 705/3 |
| 6,266,645 B1 * | 7/2001 | Simpson | 705/3 |
| 6,283,761 B1 * | 9/2001 | Joao | 434/236 |
| 6,289,088 B1 | 9/2001 | Bruno et al. | |
| 6,302,844 B1 * | 10/2001 | Walker et al. | 600/300 |
| 6,356,874 B1 | 3/2002 | Ohrn | |
| 6,542,905 B1 * | 4/2003 | Fogel et al. | 707/200 |
| 2002/0072911 A1 * | 6/2002 | Kilgore et al. | 704/270 |
| 2002/0107769 A1 * | 8/2002 | Dashefsky et al. | 705/35 |

* cited by examiner

METHOD AND A SYSTEM FOR EFFECTING TRANSFER OF A PATIENT FROM A HOSPITAL VIA A COMPUTER NETWORK

This application is a Continuation-In-Part Application of U.S. patent application Ser. No. 09/544,508 filed on Apr. 6, 2000 now U.S. Pat. No. 7,539,623.

BACKGROUND OF THE INVENTION

The present invention generally relates to a method and a system for effecting transfer of a patient from a hospital via a computer network. Further, the present invention relates to a method and a system having a transfer request form created by the hospital and stored in a database which is accessible via the computer network. An agent effecting transfer of the patient from the hospital may access the database via the computer network and may effect transfer of the patient via the computer network.

It is, of course, generally known to provide databases having information thereon. The information may be stored within the database for accessing the information at a later time. Further, it is generally known to provide access to databases on a computer network, such as, for example, the internet. A website may be utilized to simultaneously provide access to the database for adding information to the database and for retrieving information from the database.

Known methods of moving patients to beds in medical health facilities generally involve the placing of a telephone call or sending a telefax to a medical health facility to determine if a bed or a plurality of beds is available for one or more patients. Further, known methods involve asking a plurality of questions to a representative of the medical health facility to determine types of beds available, types of services offered, payment method accepted and/or other information. These questions must be asked at each facility contacted to determine which facility best suits the patient. Moreover, many times, discharge personnel, doctors and/or nurses must contact the medical health care facilities to gather the information about each facility. This may require discharge personnel, doctors and/or nurses to spend more time performing an administrative task and less time providing care and support to patients and family members' often regarding difficult and serious life and/or other health-related decisions.

Further, it is generally known to provide a website having access to a database wherein the database denotes whether beds are available at a healthcare facility. However, known websites and databases do not provide a mechanism for a user to directly contact the healthcare facilities to make appointments, to reserve a bed or beds and/or to gather further information about the facility.

Further, known databases and websites provide no information on the types of beds available, the quantity of beds available and/or a forecast of what beds may be available and when beds may be available in the future. Moreover, known databases and websites do not provide healthcare facilities access to the databases for adding or changing information regarding bed availability.

It is generally known that a patient receiving medical treatment at a hospital is often transferred to a healthcare facility after the medical treatment at the hospital is completed. Often, a hospital will refer a patient to an inappropriate healthcare facility to increase bed availability and revenue at the hospital. Also, a hospital may refer a patient to an inappropriate healthcare facility to minimize the stay of the patient at the hospital. The inappropriate healthcare facility will accept the patient to increase revenues at the healthcare facility. The healthcare facility depends on reimbursement dollars from an insurance carrier of the patient for accepting the patient which increases the revenues at the healthcare facility. However, the insurance carrier often will not reimburse the healthcare facility if the healthcare facility is inappropriate for the patient.

To guarantee reimbursement from the insurance provider of the patient, the healthcare facility and the hospital require the transfer to be approved by an agent of the insurance provider or a government agency, such as, for example, an agent of the Center for Medicare and Medicaid Services (hereinafter "the CMS agent"). The current approval process requires the hospital to send a transfer request to the agent via telefax. The agent makes a decision effecting the transfer request. If the transfer request is approved, a approval number is sent to the hospital and healthcare facility via telefax. Further, the approval number may include, for example, a numeric sequence, an alphabetic sequence and/or a sequence having both numerals and alphabetic letters. The approval number indicates that the insurance provider will reimburse the hospital for discharging the patient and the healthcare facility for accepting the transfer of the patient. However, the agent may receive thousands of the transfer requests per day resulting in a long delay before the agent makes a decision on the transfer request.

A need, therefore, exists for an improved method and a system for effecting transfer of a patient from a hospital via a computer network that overcome the problems associated with known methods and systems.

SUMMARY OF THE INVENTION

The present invention generally relates to a method and a system for effecting transfer of a patient from a hospital via a computer network. More specifically, the present invention relates to a method and a system effecting transfer of the patient from the hospital via computer network which allows the hospital to create an transfer request form on-line via a computer network. Further, the transfer request form is accessible on-line for review and/or action by an agent for an insurance provider via the computer network. Still further, the transfer request form may contain information, such as, for example, medical information, current treatment information and/or treatment need information upon discharge to a healthcare facility. A notification may be generated on-line by the agent and/or may be sent to each of the parties involved with the transfer of the patient from the hospital to the healthcare facility. Moreover, the notification indicates whether the agent approved or rejected the transfer request.

To this end, in an embodiment of the present invention, a method for receiving an approval of a reimbursement guarantee to a healthcare facility for a transfer of a patient with a condition to a healthcare facility on a computer network wherein the healthcare facility has accommodations is provided. The method comprising the steps of providing a computer network and providing a database connected to the computer network wherein the database includes facility information associated with the accommodations of the healthcare facility. The method has the step of inputting a transfer request information for the patient into the database by a hospital via the computer network wherein the transfer request information is associated with the condition of the patient. Additionally, the method has the step of providing a first access to the database for viewing the transfer request information and the facility information by a user of the database via the computer network. Further, the method has the step of determining suitability of the accommodations of the healthcare facility to the condition of the patient by the user. Moreover, the method has the step of inputting the suitability of the accommodations of the healthcare facility to the condition of the patient into the database by the user via the computer network wherein the approval of the reimbursement for the patient is based on the suitability of the accommodations of the healthcare facility to the condition of the patient.

In an embodiment, the computer network is the internet.

In an embodiment, the first access to the database is wireless.

In an embodiment, the method further has the step of communicating a notice to the healthcare facility and the hospital via the computer network wherein the notice is associated with the suitability of the accommodations of the healthcare facility to the condition of the patient.

In an embodiment, the method further has the step of notifying a transporter of the suitability of the accommodations of the healthcare facility to the condition of the patient to the healthcare facility via the computer network.

In an embodiment, the method further has the steps of providing a remote server and storing the database on the remote server.

In an embodiment, the method further has the step of providing a second access to the database for viewing the transfer request information by the healthcare facility and the hospital via the computer network wherein the transfer request information is associated with the suitability of the accommodations of the healthcare facility to the condition of the patient.

In an embodiment, the method further has the step of inputting the facility information into the database by the healthcare facility via the computer.

In an embodiment, the method further has the step of providing codes to the healthcare facility and the hospital for the approval of the reimbursement for the transfer of the patient with the condition to the healthcare facility via the computer network.

In an embodiment, the method further has the step of providing a form on a computer website for inputting the transfer request information into the database wherein the computer website is remote with respect to the database.

In an embodiment, the user is an agent of an insurance provider for the patient.

In an embodiment, the first access to the database is a hyperlink in a webpage on the computer network.

In an embodiment, the method further has the step of scheduling an interview of the patient via the computer network wherein the interview determines the suitability of the accommodations of the healthcare facility to the condition of the patient by the user.

In an embodiment, the method further has the step of granting permissions to the hospital and the healthcare facility for inputting the suitability of the accommodations of the healthcare facility to the condition of the patient into the database via the computer network.

In another embodiment of the present invention, a system for requesting a reimbursement for a transfer of a patient with a condition from a hospital to a healthcare facility on a computer network wherein the healthcare facility has accommodations is provided. The system has a computer network and a database associated with the computer network. Additionally, the system has means for inputting transfer request information into the database wherein the transfer request information is associated with the condition of the patient and the accommodations of the healthcare facility. Further, the system has means for accessing the transfer request information and modifying the transfer request information from the database. Moreover, the system has means for determining if the reimbursement is approved based on the transfer request information from the database.

In an embodiment, the computer network is the internet.

In an embodiment, the system has means for scheduling an interview of the patient via the computer network wherein the means for determining if the reimbursement is approved is based on the interview.

In an embodiment, the system has notifications delivered to the hospital and the healthcare facility via the computer network wherein the notifications are associated with the means for determining if the reimbursement is approved.

In an embodiment, the system has a remote server wherein the database is contained on the remote server and a website providing access to the database.

In an embodiment, the system has codes delivered to the hospital and the healthcare facility via the computer network wherein the codes are associated with the condition of a patient.

In an embodiment, the system has an approval number delivered to the hospital and the healthcare facility via the computer network wherein the approval number is associated with the reimbursement for the transfer of a patient from the hospital to the healthcare facility.

It is, therefore, an advantage of the present invention to provide a method and a system for effecting transfer of a patient from a hospital via a computer network.

A further advantage of the present invention is to provide a method and a system for effecting transfer of a patient from a hospital via a computer network which allows a transfer request form for discharge from a hospital to be sent on-line to a CMS agent.

Another advantage of the present invention is to provide a method and a system for effecting transfer of a patient from a hospital via a computer network which allows a CMS agent to make an on-line decision whether to transfer a patient to a facility or a healthcare provider based on a medical necessity of the patient and/or to notify the facility of reimbursements for the caring of the patient based on the medical necessity of the patient.

And, another advantage of the present invention is to provide a method and a system for effecting transfer of a patient from a hospital via a computer network which allows the CMS agent to access a on-line transfer request form and/or a specific on-line transfer request form of a government entity for review and action.

Yet another advantage of the present invention is to provide a method and a system for effecting transfer of a patient from a hospital via a computer network which allows a transportation resource, a hospital, a CMS agent and/or a healthcare resource in a community to access, view and/or modify the on-line transfer request form via the computer network.

A further advantage of the present invention is to provide a method and a system for effecting transfer of a patient from a hospital via a computer network which allows the CMS agent to take on-line action on the on-line transfer request form on-line via a computer network.

A still further advantage of the present invention is to provide a method and a system for effecting transfer of a patient from a hospital via a computer network which allows a CMS agent to make an on-line decision to approve or reject the transfer request via a computer network.

Moreover, an advantage of the present invention is to provide a method and a system for effecting transfer of a patient from a hospital via a computer network which allows the CMS agent to schedule an interview with the patient and designate and/or automatically notify an interviewer on-line via a computer network.

And, another advantage of the present invention is to provide a method and a system for effecting transfer of a patient from a hospital via a computer network which allows on-line notifications of a determination made by the CMS agent on the transfer request form to be sent to a transportation resource, a hospital, and/or the healthcare facility or other healthcare provider.

Yet another advantage of the present invention is to provide a method and a system for effecting transfer of a patient from a hospital via a computer network which allows an approval number, Medicare and/or Medicaid reimbursement codes and/or an amount of allowed reimbursement dollars to be included in the on-line notifications.

Another advantage of the present invention is to provide a method and a system for effecting transfer of a patient from a hospital via a computer network which allows a CMS agent to view history of past actions on the transfer request form on-line via the computer network.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention relates to a method and a system for effecting transfer of a patient from a hospital via a computer network. Specifically, the present invention relates to a method and a system for effecting transfer of a patient from the hospital via computer network which allows the hospital to create an transfer request form on-line via a computer network. Further, an agent for an insurance provider and/or a CMS agent may access the transfer request form on-line and/or act on the transfer request form on-line via the computer network. A notification from the agent may be sent to each of the parties involved with the transfer of the patient from the hospital to the healthcare facility and/or healthcare provider via the computer network. Further, the notification may indicate whether the agent approved or rejected the transfer request.

Figure 1:
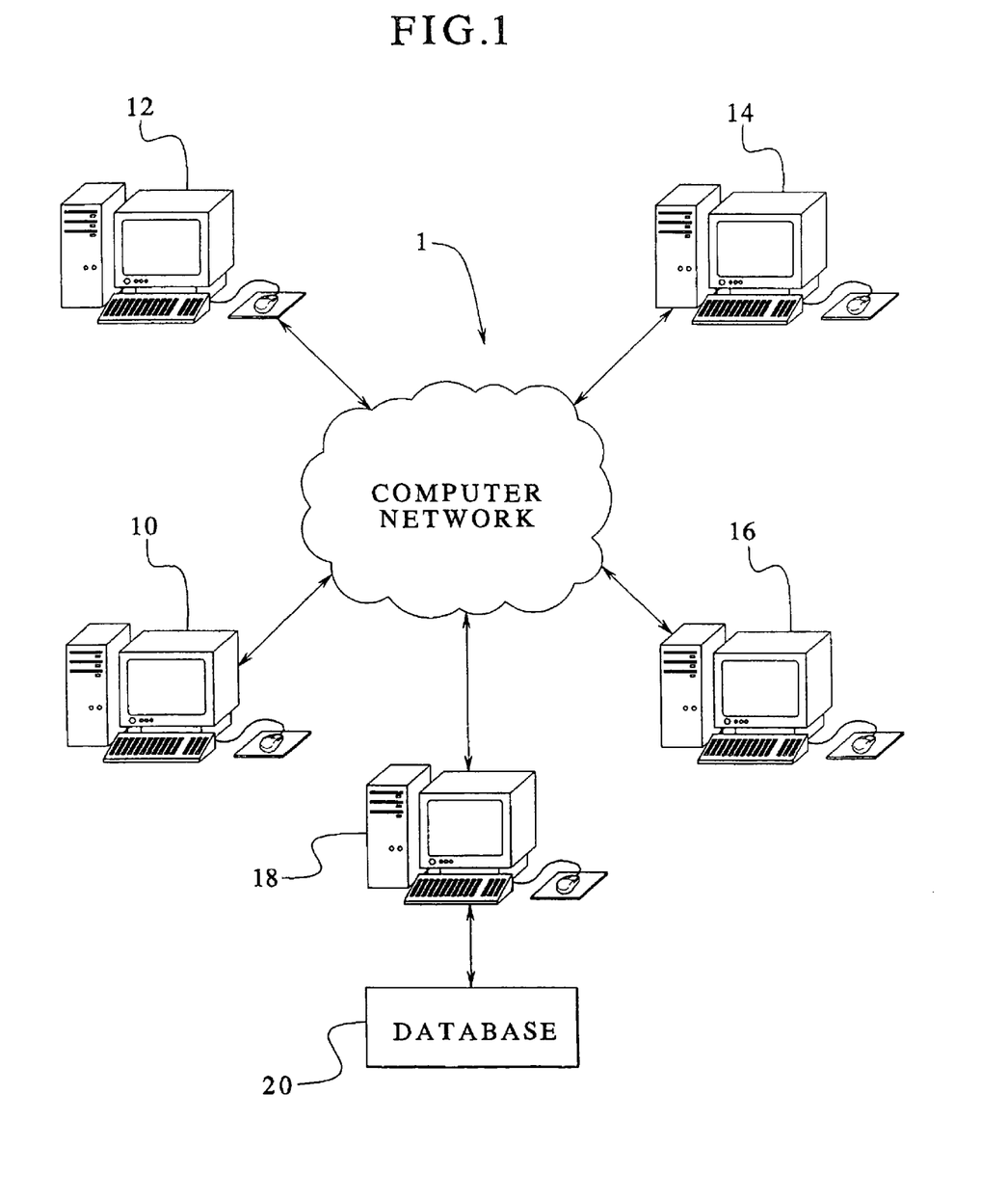
FIG. 1 illustrates a diagram of interconnected computers and a database in an embodiment of the present invention.

Referring now to the drawings wherein like numerals refer to like parts, FIG. 1 illustrates a computer network 1 having a plurality of computers 10-16 connected thereto. Further, the computer network 1 may include a server computer 18 having a database 20 attached thereto.

The computer network 1 may be any type of computer network that may interconnect a plurality of computers 10-16. Of course, any number of computers may be connected to the computer network and the invention should not be construed as limited as herein described. Further, the computer network 1 may be, for example, the internet wherein a plurality of remote computers are connected via a telephone network or other like network to each other. In addition, the computer network 10 may be an intranet wherein the plurality of computers 10-16 are connected via a network internal to an organization, such as a business, institution or the like. For example, the network may be connected via a LAN network. However, any computer network may be utilized that may be apparent to those skilled in the art.

The server computer 18 may include the database 20 associated therewith. The database 20 may contain information input into the database relating to bed availability information of healthcare providers. Any healthcare facility having bed availability information may use any of the computers 10-16 or any other computer connected via the computer network 1 to access the database 20 through the computer network 1. The healthcare facility may then enter the bed availability information into the database 20. A user of the database 20 desiring information concerning the availability of beds in a plurality of healthcare facilities could use any of the computers 10-16 or any other computer to access the database 20 and to extract the information concerning the availability of the beds of any of the healthcare facilities stored therein. The network 1, therefore, allows for real time updates and access to those updates regarding bed availability as a patient is checked in and subsequently checked out of the facility.

Further, any of the computers 10-16 may be a wireless system whereby the computer network may be accessed from a remote location. For example, any of the computers 10-16 may be a Palm Pilot by 3Com, Inc. that may access the internet wirelessly. Further, any of the computers 10-16 may be a wireless telephone having access to the internet.

Figure 2:
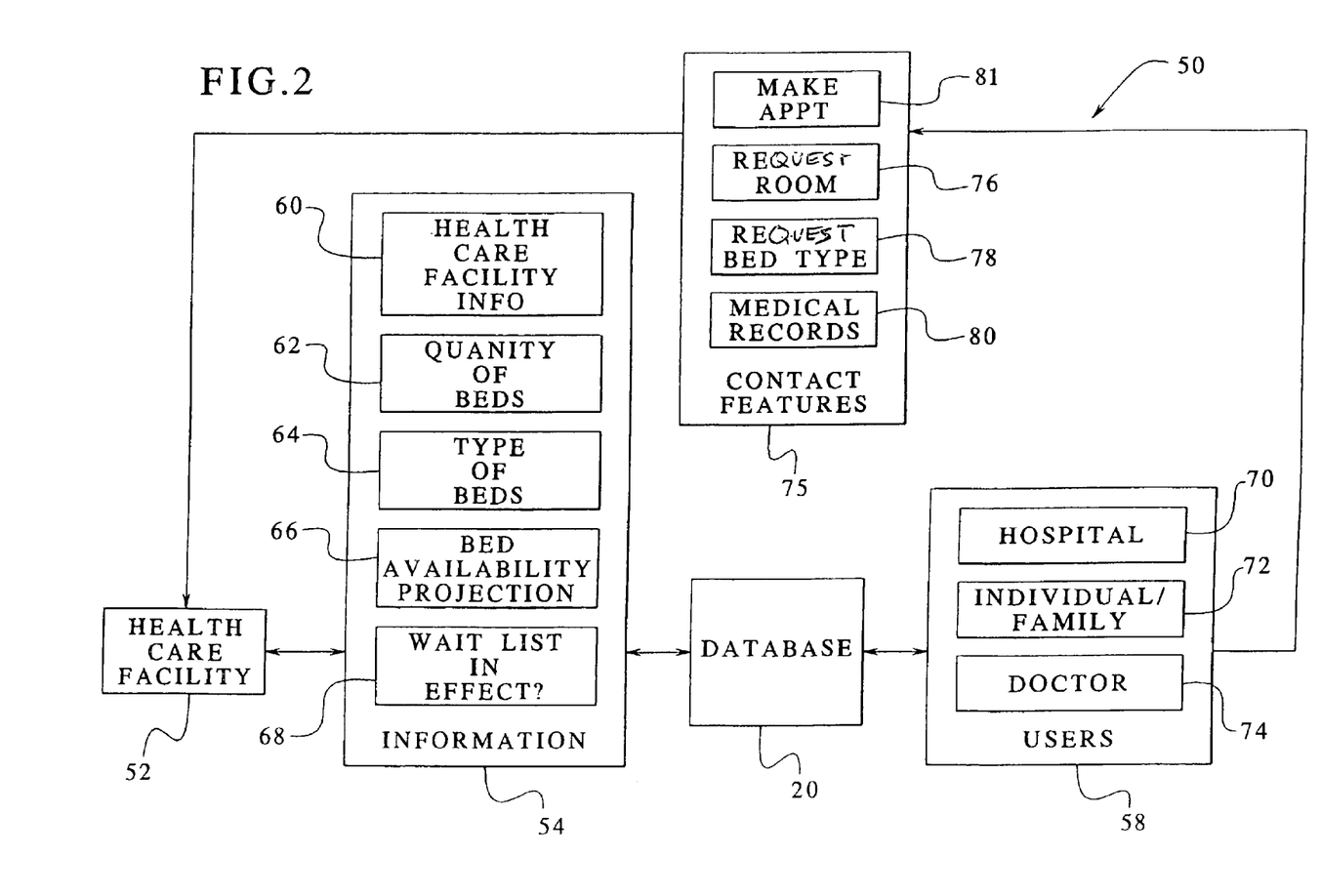
FIG. 2 illustrates a black box diagram of a healthcare provider and information that may be input into the database in an embodiment of the present invention.

FIG. 2 illustrates a black box diagram of a system 50. The system 50 includes a healthcare facility 52. Of course, any number of healthcare facilities may be included in the system 50. The healthcare facility 52 may be any type of healthcare facility, such as, for example, an assisted living facility, a home care facility, a nursing home facility, a geriatric rehabilitation facility, a continuing care facility, a hospice facility and/or a retirement home facility. Further, any other type of healthcare facility may be included in the present invention and is not meant to be limited as herein described.

The healthcare facility 52 may provide information to the database 20 for a plurality of users 58 to download. The information 54 may include healthcare facility information 60, a quantity of beds 62 in the healthcare facility 52, types of beds 64 in the healthcare facility 52, a bed availability projection 66 in the healthcare facility 52 and whether a wait-list 68 is in effect in the healthcare facility 52. Further, any other information may be provided by the healthcare facility 52 to the database 20 as may be apparent to those skilled in the art.

The healthcare facility information 60 may include a map, contact information, details of the healthcare facility 52 and/or a history of the healthcare facility 52. In addition, any other type of information may be provided about the healthcare facility 52 that may be apparent to those skilled in the art to be stored in the database 20.

The types of beds 64 available in the healthcare facility 52 may include any type of bed that the healthcare facility offers, such as, for example, beds suited for Alzheimer's disease patients, beds for intermediate care, beds with ventilators, beds in isolation, beds in negative air isolation, beds for males or females, single beds and/or luxury beds. Of course, other types of beds may be provided by the healthcare facilities that may be apparent to those skilled in the art.

The bed availability projection 66 may provide information concerning what the status of empty beds at a particular healthcare facility 52 may be in the future. For example, if the healthcare facility 52 has every bed full, the healthcare facility 52 may provide information that the a bed or a particular type of bed may be available within, for example, the following seven days. Of course, the bed availability projection 66 may provide information concerning the availability of beds at a healthcare facility for any specified time into the future such as, for example, days or weeks into the future.

The users 58 may have access to the database and may retrieve the information 54 from the database 20. The users may include a hospital 70, an individual or a family 72 and/or physicians 74. However, the users 58 may include anyone who desires to retrieve the information 54 about the healthcare facility 52 from the database 20, and the present invention should not be construed as limited as herein described.

Upon receiving the information 54 about the healthcare facility 52 from the database 20, the user 58 may then contact the healthcare facility 52 via one of the contact features 75. The user 58 may, for example, request a room 76, request a bed type 78, transfer medical records 80 to the healthcare facility 52 and/or make an appointment 81 with the healthcare facility 52. Moreover, the user 58 may contact the healthcare facility for any other reason that may be apparent to those skilled in the art.

The database 20 may be contained on a website or other graphical interface on the computer network that may provide electronic forms for the healthcare facility 52 to enter the information 54 into the database 20 or for the users 58 to obtain the information 54 from the database 20. Further, the healthcare facility 52 or the user 58 may have a website ID number and/or a password to maintain privacy and/or to change and save information input into the database 20 or taken from the database 20. The database 20 may be accessed via a single website or via a plurality of websites that are linked to the database 20.

Figure 3:
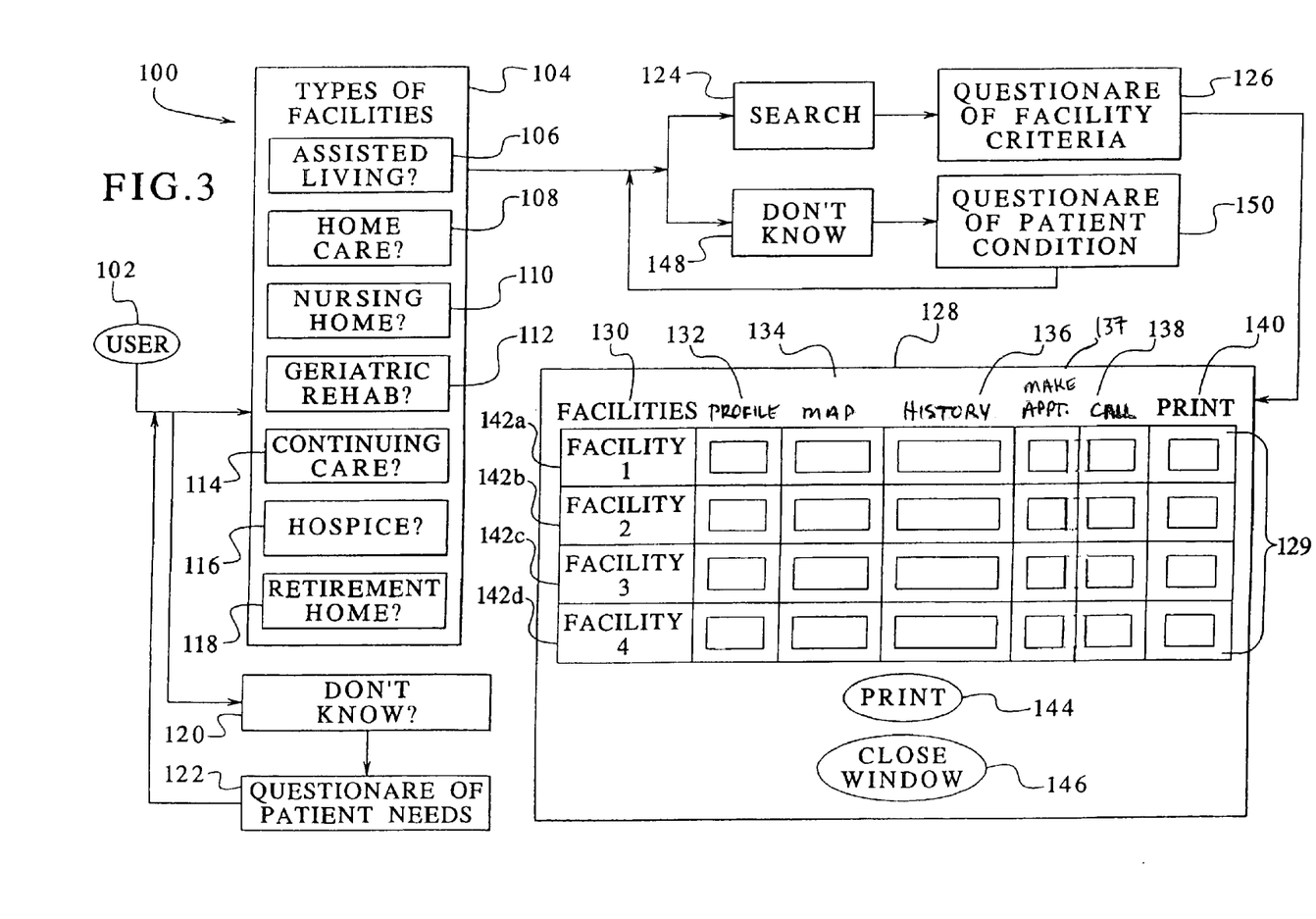
FIG. 3 illustrates a black box diagram of a decision tree and a results screen in an embodiment of the present invention.

FIG. 3 illustrates a navigation tree 100 whereby an individual user 102 may access a website or other graphical interface to begin the process of choosing a healthcare facility. The user 102 may choose from a plurality of types of facilities 104. The types of facilities 104 may include, for example, assisted living facilities 106, home care facilities 108, nursing home facilities 110, geriatric rehabilitation facilities 112, continuing care facilities 114, hospice facilities 116 and/or retirement home facilities 118. Further, any other healthcare facility may be included in the types of facilities 104 that may be apparent to those skilled in the art.

If, however, the user 102 does not know which type of healthcare facility 104 he or she may need, the user 102 may hit a "DON'T KNOW" button 120 within the graphical interface. The "DON'T KNOW" button 120 may then link the user 102 to a questionnaire of patient needs 122 whereby the user 102 answers a plurality of questions regarding the needs of the patient to be placed in the facility. The questionnaire of patient needs 122 may help the user 102 choose a type of facility that may be suited to the patient. Of course, the user 102 may be the patient seeking the type of facility. Alternatively, the user 102 may be an individual helping another in determining what type of facility may be best for the other.

The questionnaire of patient needs 122 may then be analyzed to determine and/or to recommend the type of facility needed by the user 102. The website may then link the user 102 to the particular type of facility that is recommended after answering the questions. Alternatively, the graphical interface may link the user 102 back to the types of facilities 104 thereby presenting the user 102 with the choice of the type of facilities the user 102 may desire.

The user 102 may choose a type of facility best suited for the user 102 or for another. After choosing one of the types of facilities 104, the user 102 may then search the database 20 via a search command 124 to find a particular facility or a plurality of facilities best suited for the user 102. The search command 124 may link the user 102 to a questionnaire of facility criteria 126 having a series of questions designed to find an individual facility or a plurality of facilities that match the particular criteria of the user 102.

For example, the questionnaire of facility criteria 126 may ask the user 102 to narrow the search to a particular geographic area. Further, the user 102 may input other information, such as, for example, concerning the payment method, type of facility, type of ownership, religious affiliation, population served, languages spoken, acceptance criteria, special units needed, service category needed, services needed and/or relationship with other entities. Further, other information may be used to narrow the choice of facility to one or any other number for the user 102 to choose.

After the user 102 inputs information into the questionnaire of facility criteria 126 and submits the information, a results window 128 may appear to show which facilities match the particular criteria of the user 102. The results screen 128 may include a table 129 showing facilities 130, profiles of the facilities 132, a map to the facility 134, a history of the facility 136, an option to make appointment 137, a call option 138 that allows the computer to immediately connect the user 102 to the facility via a telephone or telephone utility contained within the computer, or an option to print the information 140. The results screen 128 may include a facility 1(142a), a facility 2(142b) a facility 3(142c), a facility 4(142d) or any other facility that may be apparent to those skilled in the art that is matched by the search command 124.

The results screen 128 may include a print button 144 that may print the information of the facilities 130 as shown on the results screen 128. Further, the results screen 128 may include a "close window" button 146 that may close the results screen 128 of the graphical interface when the user 102 is finished viewing and/or printing the results screen 128. Still further, the user 102 may save the results of the search to easily access the results at a later time. In addition, the user 102 may compile lists of "favorite" healthcare facilities and save the lists in the database 20 to access at a later time.

Before the user 102 searches the database 20, the user 102 may desire a better understanding of how to match a patient's condition with the facility criteria. Therefore, a "DON'T KNOW" button 148 may be provided that may allow the user 102 to answer a plurality of questions in a questionnaire of patient condition 150. The questionnaire of patient condition 150 may include a plurality of questions related to the condition of the patient. An analysis of the answers to the questionnaire of patient condition 150 may be conducted to indicate to the user 102 what particular criteria the user 102 may be looking for in a particular facility. Further, the website may automatically search the database 20 for matching healthcare facilities based on the answers to the questionnaire of patient condition 150.

As indicated previously, the user 102 may be connected with the particular facility 130 to reserve a room 76, to reserve a bed type 78, to securely send medical records 80 thereto and/or to make an appointment 81 with the facility (as shown in FIG. 2).

Still further, if the user 102 decides to view the details 136 of the facility 130, the details 136 may indicate to the user 102 the quantity of beds provided, the types of bed provided, a bed availability projection or whether a wait-list is in effect for that facility 130. The user 102 may then use this information to find a bed in the particular facility 130 best suited for the user 102.

Figure 4:
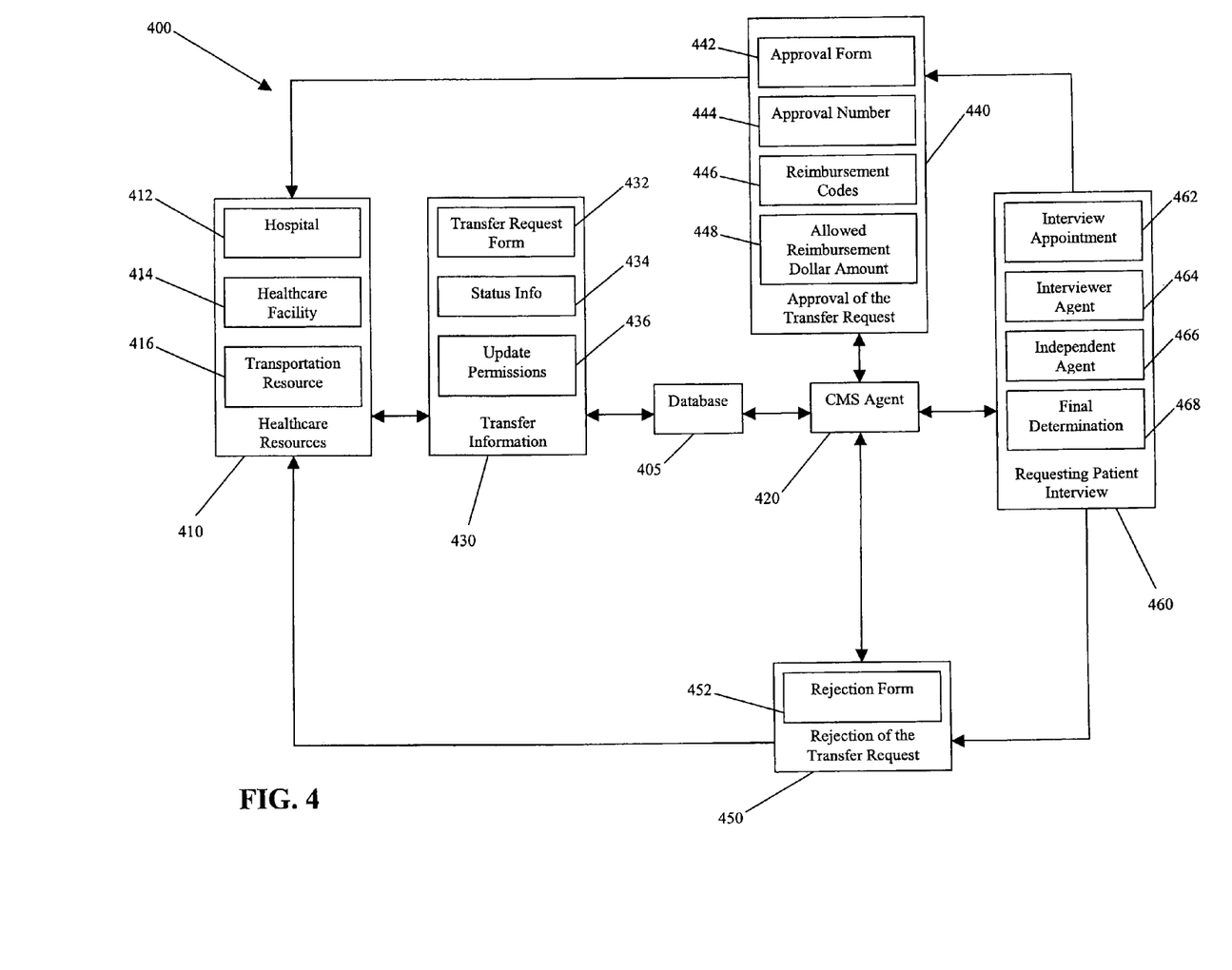
FIG. 4 illustrates a diagram of interconnected parties effecting transfer of the patient and the database in an embodiment of the present invention.

In another embodiment of the present invention, FIG. 4 illustrates a black box diagram of a system 400. The system 400 may include healthcare resources 410, which may include, for example, a hospital 412 seeking to transfer a patient with a condition to a healthcare facility 414. The healthcare facility 414 may be any type of healthcare entity, such as, for example, an assisted living facility, a home care facility, a nursing home facility, a geriatric rehabilitation facility, a continuing care facility, a hospice facility, a retirement home facility, a home healthcare agency and/or the like. The healthcare resources 410 may include a transportation resource 416 which may complete the transfer of the patient to the healthcare facility 414 by transporting the patient from the hospital 412 to the healthcare facility 414. The transportation resource 416 may be, for example, an ambulance service and/or another vehicle, such as, for example, an airplane, helicopter, ship or any combination thereof. It should be understood that the system 400 may include more than one hospital 412, healthcare facility 414 and/or transportation resource 416. Moreover, any other type of healthcare facility 414, such as, for example, the continuing care facility and/or transportation resource 416, such as, for example, the ambulance service may be used with the present invention. The present invention should not be deemed as limited to the embodiments of a specific healthcare facility and/or a specific transportation resource.

The hospital 412 may have provided the necessary medical treatment to the patient with the condition, but the patient with the condition may require further medical attention for the condition. If further medical attention for the condition is required, the patient may be transferred from the hospital 412 to the healthcare facility 414 to receive the medical attention. However, the healthcare facility 414 may require the entity that receives the patient to be approved for reimbursement by an agent for the insurance provider of the patient. The insurance provider may be, for example, a private insurance provider, such as, for example, BlueCross/BlueShield and/or the like. Further, the insurance provider may be, for example, a government agency, such as, for example, the Center for Medicare and Medicaid Services administering health and welfare programs, such as, for example, Medicare, Medicaid and/or the like. Still further, the agent for the insurance provider of the patient may be an agent 420 of the Center for Medicare and Medicaid Services (hereinafter "the CMS agent 420").

A decision to approve the transfer of the patient may be made by the CMS agent 420 and/or may establish that the healthcare facility 414 has appropriate accommodations for the needs of the patient. The decision to approve the transfer by the CMS agent 420 may establish that the healthcare facility 414 is a CMS certified Medicare and/or Medicaid facility. Additionally, the approval of the transfer by the CMS agent 420 may establish that there is a medical necessity for the patient to be transferred to the facility 414. Further, the approval of the transfer by the CMS agent 420 may assure that the healthcare facility 414 receives reimbursement dollars from Medicare and/or Medicaid for the patient. The CMS agent 420 may be any party contracting with the Center for Medicare and Medicaid Services. The management, coordination and/or disburse reimbursement dollars, such as, for example, a State Public Health Department, a State contractor, a State agency, a profit contractor and/or a non-profit contractor.

The healthcare resources 410 may provide information to a database 405 to download. The database 405 may be provided on a website or other graphical interface on the computer network that may provide electronic forms for the healthcare resources 410 to enter the information into the database 405 and/or to obtain the information from the database 405. Further, the healthcare resources 410 and/or the CMS agent 420 may have a website ID number and/or a password to maintain privacy and/or to change and save information input into the database 405 and/or taken from the database 405. The database 405 may be accessed via a single website or via a plurality of websites that are linked to the database 405.

The database 405 may be accessed by the healthcare resources 410 and/or the CMS agent 420 via a computer network which may be any type of computer network that may interconnect a plurality of computers. Of course, any number of computers may be connected to the computer network and the invention should not be construed as limited as herein described. The computer network may be, for example, the internet wherein a plurality of remote computers are connected via a telephone network or other like network to each other. In addition, the computer network 10 may be an intranet wherein the plurality of computers are connected via a network internal to an organization, such as, for example, a business, an institution and/or the like. For example, the network may be connected via a LAN network.

Further, the access to the database 405 via the computer network may be a wired access, such as, for example, telephone modem access, cable modem access, DSL access, T1 access and/or the like. Still further, the access to the computer network may be a wireless access, such as, for example, wireless Ethernet card access, Wi-Fi access or any wireless access transmits and receives signals in the radio band. However, any computer network and/or any access to the computer network may be utilized that may be apparent to those skilled in the art.

The hospital 412 may provide transfer information 430 of the patient to the database 405 for the CMS agent 420 to review. The database 405 may be contained on a website and/or other graphical interface on the computer network. The CMS agent 420 may access the transfer information 430 in the database 405 on the computer network by, for example, clicking on a hyperlink on the website and/or the like. The CMS agent 420 may review the transfer information 430 prior to making a decision to approve or to reject a request for transfer of the patient with the condition from the hospital 412 to the healthcare facility 414. The transfer information 430 may include a transfer request form 432. The transfer request form 432 may be a form, such as, for example, an Inter-Agency Transfer Form and/or status information 434. Moreover, it should be understood that the system 400 may include the transfer information 430 for any number of patients.

The database 405 may include the transfer request form 432 which may be accessed on-line by a computer in the hospital 414 via the computer network. Further, the transfer request form 432 may include patient information and/or healthcare facility information. Moreover, the transfer request form 432 may include any other information which the CMS agent 420 finds relevant to making the decision whether the transfer request form 432 of the patient is approved or rejected.

The patient information may include information relating to the patient requesting transfer from the hospital 412 to the healthcare facility 414. The healthcare facility information may include information relating to the healthcare facility 414 requesting to receive the patient after an approval of the transfer request 440. The healthcare facility information may include information, such as, for example, a name of the healthcare facility 414, an address of the healthcare facility 414 and/or contact information of the healthcare facility 414. Still further, the patient information and/or the healthcare facility information may be automatically entered into the transfer request form 432, for example, by a computer in the hospital 412 via the computer network. Alternatively, the patient information and/or the healthcare facility information may be manually entered into the transfer request form 432 an employee of the hospital 412 on the computer in the hospital 412 via the computer network.

The transfer request form 432 which has been completed by the hospital 412 may be sent to the database 405 via the computer network by, for example, an electronic mail service and/or the like. Further, the transfer request form 432 may be stored in the database 405. A request notification including information relating to the transfer request form 432 stored in the database 405 may be sent to the CMS agent 420 via the computer network by, for example, the electronic mail service, a wireless pager service and/or the like. Further, the CMS agent 420 may access and/or view the notification including the information relating to the transfer request form 432 via the computer network. Still further, the CMS agent 420 may access the transfer request form 432 in the database 405 and/or view the transfer request form 432 on the database 405 via the computer network 1. Moreover, the CMS agent 420 may make a determination on the transfer request form 432 or refrain from making the determination until the processing of the transfer request form 432 is scheduled.

The determination made by the CMS agent 420 may include approval of the transfer request 440, rejection of the transfer request 450 and/or requesting a patient interview 460. The CMS agent 420 may review the patient information and/or the healthcare facility information of the transfer request form 432 before acting on the transfer request form 432. The determination by the CMS agent 420 may be determined if the accommodations of the healthcare facility 414 are appropriate for the needs of the patient with the condition. Moreover, the determination by the CMS agent 420 may be made by the CMS agent 420 deciding whether the healthcare facility 414 may accommodate a need, such as, for example, one or more medical needs, of the patient.

The healthcare facility 414 which may accommodate the needs of the patient may be appropriate for the transfer of the patient with the condition from the hospital 412 to the healthcare facility 414. Alternatively, the healthcare facility 414 which is unable to accommodate the needs of the patient may be inappropriate for the transfer of the patient with the condition from the hospital to the healthcare facility. The CMS agent 420 may need additional information about the patient before determining if the accommodations of the healthcare facility 414 are appropriate for the needs of the patient. Further, the additional information may be required for a patient which is, for example, legally incapacitated.

The healthcare facility 414 which has been determined to be appropriate for the patient may allow the CMS agent 420 to grant the approval of the transfer request 440. The approval of the transfer request 440 may include approval information, such as, for example, an approval form 442, an approval number 444, reimbursement codes 446, an allowed reimbursement dollar amount 448 and/or the like. The CMS agent 420 may generate the approval form 442 via the computer network. The CMS agent 420 may assign the approval number 444 to the approval of the transfer request 440. Further, the approval number 444 may include, for example, a numeric sequence, an alphabetic sequence and/or a sequence including numerals and alphabetic letters. Further, the CMS agent 420 may include the reimbursement codes 446 with the approval of the transfer request 440 which may be recognized by Medicare and/or Medicaid. Still further, the CMS agent 420 may include the allowed reimbursement dollar amount 448 with the reimbursement codes 446. Moreover, the approval of the transfer request 440 may be sent to and/or stored in the database 405 via the computer network.

The approval form 442 may include information to complete the transfer of the patient with the condition from the hospital 412 to the healthcare facility 414.

The approval form 442 may include a date in which the patient is to be discharged from the hospital 412 and/or transferred to the healthcare facility 414. Further, the approval form 442 may include instructions for the transportation resource 416, such as, for example, a date and/or a time to pick-up the patient from the hospital 412, the location of the healthcare facility 414 and/or needs of the patient during transport to the healthcare facility 414. Moreover, the approval form 442 may include any other information which the CMS agent 420 may find relevant to complete the transfer of the patient with the condition from the hospital 412 to the healthcare facility 414.

The approval number 444 may indicate to the healthcare resources 410 that, for example, the transfer request form 432 of the patient has been approved by the CMS agent 420. Further, the approval number 444 may indicate to the healthcare resources 410, for example, that the healthcare resources 410 may be reimbursed by Medicare and/or Medicaid for the expenses relating to the transfer of the patient. Moreover, the approval number 444 may indicate, for example, that Medicare and/or Medicaid may provide reimbursement to the healthcare facility 414 for expenses relating to the medical treatment of the patient.

The reimbursement codes 446 and/or the allowed reimbursement dollar amount 448 may be provided to the healthcare resources 410 with the approval of the transfer request 440. The reimbursement codes 446 may be codes from treatment coding systems, procedural coding systems and/or diagnosis coding systems, such as, for example, CPT coding, ICD-9 coding, ICD-10 coding and/or the like. The reimbursement codes 446 may be submitted by one or more of the healthcare resources 410 to Medicare and/or Medicaid. Medicare and/or Medicaid may reimburse one or more of the healthcare resources 410 according to the reimbursement codes 446 submitted by the healthcare resources 410. Further, the allowed reimbursement dollar amount 448 may be calculated according to the reimbursement codes 446 which may be included with the approval of the transfer request 440 by the CMS agent 420. The allowed reimbursement dollar amount 448 may be calculated by Medicare and/or Medicaid based on the reimbursement codes 446 which may be submitted by the healthcare resources 410. Moreover, the reimbursement codes 446 may include any other coding system which Medicare and/or Medicaid accept from the healthcare resources 410.

An approval notification including the approval information in the approval of the transfer request 440 may be sent to one or more of the healthcare resources 410 via the computer network by, for example, the electronic mail service, the wireless pager service and/or the like. Further, one or more of the healthcare resources 410 may access and/or may view the approval notification including the approval information of the approval of the transfer request 440 in the database 405 via the computer network. Still further, the CMS agent 420 may access and/or may view the approval information of the approval of the transfer request 440 in database 405 via the computer network. Moreover, the CMS agent 420 may modify and/or may store the approval information of the approval of the transfer request 440 in the database 405 via the computer network.

The healthcare resources 410 may accept the patient according to the approval information of the approval of the transfer request 440. The hospital 412 may discharge the patient on the date provided in the approval form 442. The transportation resource 416 may transport the patient from the hospital 412 to the healthcare facility 414 according to the approval information in the approval form 442. The healthcare facility 414 may accept the patient and accommodate the needs of the patient in accordance to the approval information in the approval form 442. One or more of the healthcare resources 410 may submit the reimbursement codes 446 provided in the approval of the transfer request form 440 to Medicare and/or Medicaid. Further, one or more of the healthcare resources 410 may receive the allowed reimbursement dollar amount 448 provided in the approval of the transfer request 440 from Medicare and/or Medicaid.

The healthcare facility 414 determined to be inappropriate for the patient may require the CMS agent 420 to issue the rejection of the transfer request 450. The rejection of the transfer request 450 may include a rejection form 452 which provides rejection information, such as, for example, a basis for the rejection of transfer request 450, reasons for the determination if the accommodations of the healthcare facility 414 are appropriate for the needs of the patient, and/or the like. The CMS agent 420 may generate the rejection form 452 of the rejection of the transfer request 450 via the computer network. Moreover, the rejection of the transfer request 450 may be sent to and/or stored in the database 405 via the computer network. Moreover, the rejection form 452 may include any other information which the CMS agent 420 finds relevant to the rejection of the transfer request 450 of the patient.

A rejection notification including the rejection form 452 stored in the database 405 may be sent to one or more of the healthcare resources 210 via the computer network by, for example, the electronic mail service, the wireless pager service and/or the like. Further, one or more of the healthcare resources 410 may access and/or may view the rejection notification including the rejection form 452 in the rejection of the transfer request 450 on the database 405 via computer network. Still further, the CMS agent 420 may access and/or view the rejection form 452 of the rejection of the transfer request 450 on the database 405 via the computer network. Moreover, the CMS agent 420 may modify and/or store the rejection form 452 of the rejection of the transfer request 450 in the database 405 via the computer network.

The transfer request form 432 for the patient which is legally incapacitated may require the CMS agent 420 to obtain additional information about the patient by requesting the patient interview 460 via the computer network. The CMS agent 420 which is requesting the patient interview 460 may gather information to aid in the determination of whether the healthcare facility 414 is appropriate to accommodate the needs of the patient lacking capacity. Further, the patient may be lacking capacity due to a condition, such as, for example, the patient suffers from mental retardation, the patient suffers from mental illness, the patient is under the age of twenty-one (21) years old and may be attempting to qualify for Medicare and/or Medicaid and/or the like.

The CMS agent may set an on-site interview appointment 462 with the patient via the computer network. The requesting the patient interview 460 may including interview information, such as, for example, an identification of the interviewer 464 and/or a date and/or a time of the on-site interview appointment 462. Further, the CMS agent 420 may serve as the interviewer of the patient during the on-site interview appointment 462 or may designate an independent agent 466, such as, for example, Catholic Charities in the State of Illinois, to serve as the interviewer of the patient during the on-site interview appointment 462. The interviewer of the patient during the on-site interview appointment 462 may make a final determination 468 whether the healthcare facility 414 is appropriate for the patient.

An interview notification may be generated in the database 405 by the CMS agent 420 which schedules the on-site interview appointment 462. Further, the interview notification may be stored in the database 405 via the computer network. The interview notification may be sent to the hospital 412 and/or the healthcare resources 210 via the computer system by, for example, the electronic mail service, the wireless pager service and/or the like. The interview notification may include the interview information, such as, for example, the date and the time of the on-site interview appointment 462, interviewer 464 information and/or independent agent 466 information and/or the like. Still further, one or more of the healthcare resources 410 may access and/or may view the interview notification in the database via the computer network. Moreover, the hospital 412 may communicate with the CMS agent to adjust the date and the time of the on-site interview appointment 462 via the computer network.

The final determination 468 by the interviewer 464 may be the approval of the transfer request 440 or the rejection of the transfer request 450. Further, the final determination 468 may be generated in and/or stored in the database 405 via the computer network. The final determination 468 by the independent agent 466 as the interviewer 464 may be sent to the CMS agent 420 via the computer network. Still further, one or more of the healthcare resources 410 may access and/or view the final determination 468 in the database 405 via the computer network.

The final determination 468 for the approval of the transfer request 440 may require the CMS agent 420 to provide the approval information including the approval form 442, the approval number 444, the reimbursement codes 446 and/or the allowed reimbursement dollar amount 448. The final determination 468 for the approval of the transfer request 440 may require the CMS agent 420 to generate and/or store the approval notification in the database 405. Further, the approval notification may be stored in the database 405 and/or sent to one or more of the healthcare resources 410 via the computer network.

The final determination 468 for the rejection of the transfer request 450 may require the CMS agent 420 to provide the rejection information including the rejection form 452. The final determination 468 for the approval of the transfer request 440 may require the CMS agent 420 to generate and/or store the rejection notification in the database 405. Further, the rejection notification may be stored in the database 405 and/or sent to one or more of the healthcare resources 410 via the computer network. The transfer information 430 may include status information 434 of the transfer request form 432. The status information 434 may include real-time information, such as, for example, the status of the transfer request form 432, a history of past actions on the transfer request form 432 by the CMS agent 420 and/or information relating to an appeal from the rejection of the transfer request form 432 by the CMS agent 420. Moreover, the status information 434 may include any other information relating to any other actions on the transfer request form 432 which the CMS agent 420 may find appropriate.

The status information 434 of the transfer request form 432 for the patient may be entered into the transfer information 430 by the CMS agent 420 and/or may be accessed on the database 405 via the computer network. After the status information 434 has been entered into the transfer information 430 by the CMS agent 420, the status information 434 may be sent to and/or stored in the database 405 via the computer network.

The transfer information 430 on the database 405 including the transfer request form 432 and/or the status information 434 may be access by one or more of the healthcare resources 210 via the computer network. Further, the transfer information 430 may be modified by one or more of the healthcare resources 410 and/or the CMS agent 420 and may be stored in the database 405 via the computer network. A status notification including the discharge information 230 modified and stored in the database 405 may be generated and/or sent to one or more of the healthcare resources 410 and/or the CMS agent 420 via the computer network. Further, the computer network may send the status notification to one or more of the healthcare resources 410 and/or the CMS agent 420 by, for example, the electronic mail service, the wireless pager service and/or the like.

The transfer information 430 may include update permissions 436 which may permit one or more of the healthcare resources 410 and/or the CMS agent 420 to modify the transfer request form 432 and/or the status information 434. The update permissions 436 may allow, for example, the healthcare facility 414 to modify the healthcare facility information of the transfer request form 432 of the patient, the hospital 412 to modify the patient information of the transfer request form 432 of the patient and/or the like. Alternatively, the update permissions 436 may allow, for example, the CMS agent 420 to modify any information in the transfer information 430 including the transfer request form 432 and/or the status information 434. Further, the update permissions 436 may be determined based on guidelines from the Center for Medicare and Medicaid Services. Moreover, the update permissions 436 may be stored in the database 405 and/or may be applied in the system 400 via the computer network.

The system 400 may provide the transfer information 430 including the transfer request form 432 from the healthcare resources 410 which may be stored in the database 405 via the computer network. The CMS agent 420 may access and/or may view the discharge information 430 on the database 405 via the computer network. Further, the CMS agent 420 may make a determination for the approval of the transfer request 440, the rejection of the transfer request 450 and/or the requesting of the patient interview 460. The determination made by the CMS agent 420 may be stored in the database and accessed for viewing via the computer network. Further, the database 405 may include notifications for the determination made by the CMS agent 420 which may be sent to the healthcare resources 410 and/or the CMS agent 420 via the computer network. Moreover, the database 405 may be modified via the computer network by the healthcare resources 410 and/or the CMS agent 420 according to the update permissions 436.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

I claim:

1. A method for receiving an approval of a reimbursement guarantee on a computer network from an insurance provider of a patient with a medical need for a transfer of the patient from a hospital to a healthcare facility wherein the healthcare facility has a bed available to accommodate the medical need of the patient, the method comprising the steps of:
   providing a computer network;
   providing a database connected to the computer network wherein the database includes facility information associated with the bed of the healthcare facility;
   inputting a transfer request information for the patient into the database via the computer network wherein the transfer request information is associated with the medical need of the patient;
   providing a first access to the database to view the transfer request information and the facility information by the insurance provider via the computer network;
   determining a suitability of the bed of the healthcare facility to accommodate the medical need of the patient;
   determining if the transfer of the patient from the hospital to the healthcare facility is medically necessary based on the medical need of the patient; and
   inputting the suitability of the bed of the healthcare facility to accommodate the medical need of the patient into the database by the insurance provider via the computer network wherein the approval of the reimbursement guarantee for the transfer of the patient is based on the suitability of the bed of the healthcare facility to accommodate the medical need of the patient and whether the transfer of the patient from the hospital to the healthcare facility is medically necessary.

2. The method of claim 1 wherein the computer network is the internet.

3. The method of claim 1 wherein the first access to the database is effected via wireless communication.

4. The method of claim 1 further comprising the step of:
   communicating a notice to the healthcare facility and the hospital via the computer network wherein the notice is associated with the approval of the reimbursement guarantee.

5. The method of claim 1 further comprising the step of:
   notifying a transportation resource of the approval of the reimbursement guarantee via the computer network wherein the transportation resource transports the patient from the hospital to the healthcare facility.

6. The method of claim 1 further comprising the steps of:
   providing a remote server; and
   storing the database on the remote server.

7. The method of claim 1 further comprising the step of:
   providing a second access to the database to view the transfer request information by the healthcare facility and the hospital via the computer network.

8. The method of claim 1 further comprising the step of:
   inputting the facility information into the database via the computer network.

9. The method of claim 1 further comprising the step of:
   providing codes to the healthcare facility and the hospital via the computer network for the approval of the reimbursement guarantee.

10. The method of claim 1 further comprising the step of:
    providing a form on a computer website to input the transfer request information into the database wherein the computer website is remote with respect to the database.

11. The method of claim 5 wherein the transportation resource is an ambulance service.

12. The method of claim 1 wherein the first access to the database is a hyperlink in a webpage on the computer network.

13. The method of claim 1 further comprising the step of: scheduling an interview of the patient via the computer network wherein the interview determines the suitability of the bed of the healthcare facility to accommodate the medical need of the patient.

14. The method of claim 1 further comprising the step of: granting permissions to the hospital and the healthcare facility to input the suitability of the bed of the healthcare facility to accommodate the medical need of the patient into the database via the computer network.

* * * * *